(12) United States Patent
Lee et al.

(10) Patent No.: US 7,695,741 B2
(45) Date of Patent: Apr. 13, 2010

(54) TOPICAL FORMULATION FOR PREVENTION AND TREATMENT OF ACNE

(75) Inventors: Soon Keun Lee, Suwon-shi (KR); Wie-Jong Kwak, Seoul (KR); Chang-Kyun Han, Seoul (KR); Joo Hyon Kim, Seongnam-shi (KR)

(73) Assignee: SK Chemicals Co., Ltd., Kyungki-do (KR)

( * ) Notice: Subject to any disclaimer, the term of this patent is extended or adjusted under 35 U.S.C. 154(b) by 457 days.

(21) Appl. No.: 10/523,854

(22) PCT Filed: Aug. 12, 2003

(86) PCT No.: PCT/KR03/01626

§ 371 (c)(1),
(2), (4) Date: Feb. 7, 2005

(87) PCT Pub. No.: WO2004/016239

PCT Pub. Date: Feb. 26, 2004

(65) Prior Publication Data

US 2005/0271750 A1     Dec. 8, 2005

(30) Foreign Application Priority Data

Aug. 14, 2002   (KR) ................. 10-2002-0048073

(51) Int. Cl.
*A61K 36/00* (2006.01)
*A61K 9/00* (2006.01)
*A61K 47/00* (2006.01)

(52) U.S. Cl. .................. 424/725; 424/400; 424/439

(58) Field of Classification Search .............. 424/725
See application file for complete search history.

(56) References Cited

U.S. PATENT DOCUMENTS 6,419,963 B1 *   7/2002  Niazi ................ 424/757
2002/0025348 A1 * 2/2002  Basu et al. ........... 424/735

FOREIGN PATENT DOCUMENTS

| CN | 1332002 | | 1/2002 |
| JP | 355127317 A | * | 10/1980 |
| JP | 409143087 A | * | 6/1997 |
| JP | 2001089346 A | * | 4/2001 |
| KR | 10-0357824 B1 | | 10/2002 |

OTHER PUBLICATIONS

DW-ACC 2001-576146, Apr. 2001, DW ACC or KR, Park.*
DW-ACC 1995-101781, Jan. 1995, DW ACC or JP, Abe.*
Lee, Gyeong-Im; Ha, Joo Young; Min, Kyung Rak; Nakagawa, Hideo; Tsurufuji, Susumu; Chang, Il-Moo; Kim, Youngsoo; "Inhibitory Effects of Oriental Herbal Medicines on IL-8 Induction in Lipopolysaccharide-Activated Rat Macrophages", *Planta Medica*, Republic of Korea, 1995, vol. 61, No. 1, pp. 26-30.

* cited by examiner

*Primary Examiner*—Christopher R. Tate
*Assistant Examiner*—Randall Winston
(74) *Attorney, Agent, or Firm*—Frommer Lawrence & Haug LLP; Ronald R. Santucci

(57) ABSTRACT

Disclosed is a topical formulation for preventing or treating acne, in particular to a topical formulation for preventing or treating acne through the antimicrobial activity of the formulation against acne-causing bacteria, *Propionibacterium acnes*, inhibition of excess production of sebum by inhibition of excess production of sebum by inhibition of 5α-reductase, inhibition of comedo, keratolysis and anti-inflammatory action, which comprises extract obtained from at least one oriental medicine selected from the group consisting of *Cavalia gladiata*, *Biota orientalis* and *Coptis chinensis*.

5 Claims, No Drawings

TOPICAL FORMULATION FOR PREVENTION AND TREATMENT OF ACNE

This application is a 371 of PCT/KR2003/001626 filed on Aug. 12, 2003, published on Feb. 26, 2004 under publication number WO 2004/016239 A1 which claims priority benefits from South Korean Patent Application Number 10-2002-0048073 filed Aug. 14, 2002.

BACKGROUND OF THE INVENTION

1. Field of the Invention

The present invention relates to a topical formulation for preventing or treating acne through antimicrobial activity against acne-causing bacteria, *Propionibacterium acnes*, inhibition of excess production of sebum by inhibition of 5α-reductase, inhibition of comedo, keratolysis and anti-inflammatory action, which comprises extract obtained from at least one oriental medicine selected from the group consisting of *Cavalia gladiata, Biota orientalis* and *Coptis chinensis*.

2. Description of the Related Technical Field

Acne is developed in teen-agers at an incidence of 90% but also found in adults of in their twenties- or thirties at rare intervals. Acne (or acne vulgaris) is a chronic inflammatory disease or a disorder developed at sebaceous gland and hair follicle, of which etiopathology includes excess secretion of sebum, dyskeratinization of epidermis of hair follicle, overgrowth of anaerobic skin-colonizing bacterium, *Propionibacterium acnes* and other causes. Acne is generally found on face, chest, back, neck and brachium, the most noticeable parts of skin, and characterized as comedo, pustule, lupus, petty knob or scar.

At the early stage of acne, the excessively-secreted sebum is accumulated in hair follicle and the hair follicle is in turn swelled due to pressure of sebum, resulting in the occurrence of comedo, wherein those with closed hair follicle become white acnes (closed comedo) while those with slight-opened hair follicle tip become black acnes (open comedo). Upon further development of acne, bacteria elicit inflammation that contributes to the occurrence of two different types of symptoms: a papule type showing reddish skin with petty comedo and a pustule type showing pus. There are a few differences between acnes of teen-agers and adults, as summarized in Table 1.

TABLE 1

| Differences between Acnes of Teen-agers and Adults | | |
|---|---|---|
| Classification | Teen-ager acnes | Adult acnes |
| Location of Occurrence | Brow, entire face, any parts where sebaceous gland exists | Tend to position at the lower part of face such as cheek, girth of mouth and jaws as compared to teen-agers |
| Season of Occurrence | Spring and Summer in association with activation of sebaceous gland | Year-round occurrence without seasonal outbreak |
| Symptoms | Developed simultaneously with excess sebum, appearance of petty comedo at the activated part of sebum secretion | Developed simultane-ously with skin dryness, repetition of petty acne boss (shot appearance type), slow progress in treatment, vestige of acnes remained |
| Causes | Physical instability during growth period | Closely related to physical and mental conditions of body such as hormonal imbalance, insufficient sleep, fatigue, stress and menstruation. Low relation to skin conditions |

As shown in Table 1, the teen-ager acnes are developed at the entire parts of brow and face in spring and summer when the secretion of sebum is active and they are very likely to develop in oily skins. In contrast, the adult acnes are apt to develop throughout the year at restricted parts and are known to have little or no relation with lipid content. The development is affected by physical and mental conditions of body such as hormonal imbalance, stress, irregular dietary habits and poor body conditions thus implying complexity of its etiology. Even after fairly good treatment of adult acnes, it is very likely that pigmentation occurs to produce freckles and also the affected skin surface is sometimes caved in to form acne crater at the site. The hormones that have drawn much attention as known to cause adult acnes are androgen, which secretes sebum through stimulation of sebaceous gland and estrogen, the antagonist of androgen. Where the balance of two hormones is disrupted, it results in secretion of excess sebum and acne is developed as a result.

A variety of pharmaceuticals have been developed as an effort to treat acnes, which include antibiotics such as erythromycin and benzoylperoxide to inhibit a proliferation of acne-causing bacteria and estrogen to regulate sebum secretion, however, most of which are generally associated with adverse effects. In cosmetics, vitamin A derivatives to remove keratin; and trichloric acid and salicylic acid to inhibit a proliferation of acne-causing bacteria have been developed and tested. However, these active ingredients exhibit a little effect but are usually associated with adverse effects such as skin flaring, skin hypersensitivity and light hypersensitivity. Further, the recurrence of acnes are usually observed when administered with these active ingredients. Consequently, there are not genuine products capable of preventing and treating acne.

SUMMARY OF THE INVENTION

In an effort to develop a novel topical formulation for treating or preventing acnes, the present inventors have performed extensive experiments using active ingredients allegedly known to be involved in mechanism of acne treatment (antimicrobial activity, inhibition of excess production of sebum, keratolysis, anti-inflammatory action, etc.) based on the disclosures in various publications related to oriental medicines. As a result, the present inventors have found that *Cavalia gladiata, Biota orientalis* and *Coptis chinensis* are very effective in prevention and treatment of acnes and also have very little or no irritation.

Accordingly, it is an object of this invention to provide a topical formulation for preventing or treating acnes, which comprises extract obtained from at least one oriental medicine selected from the group consisting of *Cavalia gladiata, Biota orientalis* and *Coptis chinensis*.

It is another object of this invention to provide a composition of oriental medicine to exhibit therapeutic effects on acnes with little or no irritation.

DETAILED DESCRIPTION OF THIS INVENTION

The present invention is directed to a topical formulation for preventing or treating acnes, which comprises extract obtained from at least one oriental medicine selected from the group consisting of *Cavalia gladiata, Biota orientalis* and *Coptis chinensis*.

The present invention will be described in more detail hereunder:

The present invention relates to a topical formulation for preventing or treating acne through antimicrobial activity against acne-causing bacteria, *Propionibacterium acnes*, inhibition of excess production of sebum by inhibition of 5α-reductase, inhibition of comedo formation, keratolysis and anti-inflammatory action, which comprises extract obtained from at least one oriental medicine selected from the group consisting of *Cavalia gladiata, Biota orientalis* and *Coptis chinensis*.

*Cavalia gladiata* is an annual plant and belongs to Leguminosae. Since its bean hull looks like a straw cutter, it is generally called a sword bean. It has been generally cultivated in the southern part of Korea and the region of Jangriver and the southern parts of China. Its root and husk is also used as medicines. It has been known that *Cavalia gladiata* contains Vitamins A and C, a hydrolytic enzyme urease, hemmagglutinine and canavanine. It has been used since old times as raw materials for high-quality food and oriental medicine in China such as medicines for treating hiccough due to cold sweat, vomiting and stomachache. Currently, in the field of folk remedy, *Cavalia gladiata* is known to be effective in treatment of purulent diseases such ozena and hemorrhoids.

*Coptis chinensis* is a perennial herbaceous plant that belongs to the family of a buttercup and its root stem has been used from the beginning as a raw material for oriental medicines. It has been known as a safe plant because it elicits no irritation to skin and mucous membrane. *Coptis chinensis* has been reported to contain alkaloids such as berberine, coptisine, worenine, palmatine and columbamaine together with obakunone and obakulactone. It has been used in China to treat scald, purulent infection, infectious dermatis, ozena, palatum inflammation and exudative erythema multiforme, and used as raw materials of medicines for gastrointestine and intestinal disorders.

*Biota orientalis* is a seed from a *thuja* that belongs to Cupressaceae. The fresh ones look light yellow or yellowish white and old ones look yellowish brown and leak oil. Usually, *Biota orientalis* has been cultivated in various regions of China and its seed contains about 14% oil and a small amount of saponin. It has been used for treating anxieties and astriction and also as a raw material for medicines to treat inflammation and depilation as well as a calmative.

The extract of this invention may be prepared by the steps of powderizing *Cavalia gladiata, Biota orientalis* and *Coptis chinensis*, respectively, heat-extracting the powder in at least one extraction solvent selected from the group consisting of distilled water, methanol, ethanol, propanol, butanol, glycerol, propyleneglycol, 1,3-butylene glycol, methyl acetate, ethyl acetate, benzene, hexane, diethyl ether and dicholoromethane, filtering the extract, concentrating and freeze drying the resultant under reduced pressure.

The mixed extract of *Cavalia gladiata, Biota orientalis* and *Coptis chinensis* is prepared by powderizing *Cavalia gladiata, Biota orientalis* and *Coptis chinensis*, respectively, mixing the powders and extracting the mixed powders; or powderizing *Cavalia gladiata, Biota orientalis* and *Coptis chinensis*, respectively, extracting each powder and mixing the extracts.

When a mixed extract is used, the formulation of this invention comprises the extract from two different kinds of oriental medicines, where each extract comprises 0.01-10 wt % of *Cavalia gladiata* and 0.01-10 wt % of *Biota orientalis*; 0.01-10 wt % of *Cavalia gladiata* and 0.001-5 wt % of *Coptis chinensis*; or 0.01-10 wt % of *Biota orientalis* and 0.001-5 wt % of *Coptis chinensis*. In addition, the formulation comprises the extract obtained from three different kinds of oriental medicines, where each extract comprises 0.01-10 wt % of *Cavalia gladiata* and 0.01-10 wt % of *Biota orientalis*; and 0.001-5 wt % of *Coptis chinensis*. If the concentration is lower than the above range, the efficacy becomes negligible; in the case of exceeding, adverse effects on skin and the technical problems associated with formulation occur.

It is preferred that the extract from at least one oriental medicine selected from the group consisting of *Cavalia gladiata, Biota orientalis* and *Coptis chinensis* is contained in an amount of from 0.001 wt % to 20.0 wt %. If the amount is less than 0.001 wt %, the treatment efficacy is very poor; in the case of exceeding 20.0 wt %, adverse effects on skin and the technical problems associated with formulation occur.

The formulation of this invention may be in the form of emulsion, gel, pack, cosmetic liquid or soap for cosmetics, or ointments or patches for pharmaceuticals along with a pharmaceutically acceptable carrier or a vehicle. Each particular formulation may be prepared in accordance with the conventional processes.

The effective dose of the present formulation for topical administration may vary depending on shape, size, part of occurrence and age of a subject, and it is generally applied twice to several times a day.

The topical formulation of this invention comprising at least one oriental medicine selected from the group consisting of *Cavalia gladiata, Biota orientalis* and *Coptis chinensis* is very effective in the prevention and treatment of acnes.

The following specific examples are intended to be illustrative of the invention and should not be construed as limiting the scope of the invention as defined by appended claims.

EXAMPLE 1

Preparation of Extract from *Cavalia gladiata, Biota orientalis* and *Coptis chinensis*

The extracts obtained from *Cavalia gladiata, Biota orientalis* and *Coptis chinensis* used in this invention were prepared as follows:

200 g each of *Cavalia gladiata, Biota orientalis* and *Coptis chinensis* were washed with distilled water, dried and powderized with a pulverizer specially designed for oriental medicine, and to the resultant about 10-fold volume of 80% ethanol solvent were added. The extraction was performed by heating for 8 hr 80° C. using a device equipped with a cooling condenser to prevent the evaporation of a solvent. The extract was filtered through a 400-mesh filter cloth and the remainder was filtered once. Each extract from oriental medicines was cooled to room temperature and filtered through Whatman No. 2 filter paper, and the filtrate was concentrated at 48° C. under reduced pressure with a retrieving solvent evaporated by use of a distilled apparatus equipped with the cooling condenser (Buchi Rotavapor R-124, Water Bath B-480 Made in Switzerland, Eyela A-3S Tokyo rikakikai), followed by freeze drying, finally yielding 15.8 g of *Cavalia gladiata* extract, 8.9 g of *Biota orientalis* extract and 14.6 g of *Coptis chinensis* extract as dry weight.

EXAMPLE 2

Evaluation of Inhibitory Effect on 5α-Reductase

Testosterone 5α-Reductase, used to examine the inhibitory effect of the extract obtained from oriental medicines against testosterone 5α-reductase activity, was prepared at a temperature of below 4° C. The white female Sprague-Dawley rat aged at 8 weeks was anesthetized by inhalation of diethyl-ether and sacrificed by the disjunction of cervicals, followed by liver ablation. The extracted liver was washed three times with PBS (phosphate buffered saline) and 3 volumes of ice-cold buffer (50 mM sodium phosphate, pH 6.8, 0.25 M sucrose, 1 mM dithiothreitol) were added, followed by pulverizing with a cell homogenizer (Polytron Homogenizer), obtaining homogenized suspension. For isolating 5α-Reductase from the suspension thus obtained, the suspension was subject to ultrasonication for 5 min and centrifugation (15,000 rpm, 4° C., 5 min) for preparing a protein layer. The supernatant was resuspended in the buffer described above and stored at a temperature of −80° C. The protein quantification of the protein suspension obtained thus was performed according to Bradford method and its accurate value was determined with ELISA reader.

For evaluating the inhibitory effect on the activity of 5α-Reductase, to 50 μl of the reaction solution, 10 μl of ethanol solution of inhibitor or tested sample (70% ethanol solution containing extract from oriental medicine) were added and the protein suspension was added to the volume of 100 μl of the reaction solution. The reaction solution contains 50 mM $Na_2HPO_4$ (pH 6.8), 25 mM KCl, 500 mM NADPH and 50 mM (3H) testosterone. The reaction mixture was reacted in water bath for 10 min at 37° C. and 250 μl of the reagent for reaction termination (mixture of 70% cyclohexane and 30% ethylacetate) were added to terminate the reaction. To obtain steroids from the reactant terminated, the reactant was centrifuged to prepare supernatant and the supernatant was placed in hood for 1 day for evaporating the reaction solvent, after which the remainder obtained was dissolved in 20 μl of chloroform. The resultant was spotted on TLC plate and developed for 30 min with a developing solution (toluene:acetone=4:1) in TLC chamber and the plate developed was exposed for 3 days to hyperfilm. The area exposed was measured with densitometer and the inhibitory rate against testosterone 5α-Reductase was calculated as shown in the below formula 1. The results are summarized in Tables 2 and 3.

Inhibitory rate against testosterone 5α-reductase (%)= $[(A−B)/A]×100$  Formula 1 wherein A is the conversion rate of testosterone to dihydro-testosterone with no addition of a sample, and B is the conversion rate of testosterone to dihydro-testosterone with the addition of a sample.

TABLE 2

| Active ingredients | Conc. (%) | Inhibitory rate against 5α-reductase (%) |
|---|---|---|
| *Cavalia gladiata* | 0.1 | 100.0 |
| | 0.01 | 38.3 |
| *Biota orientalis* | 0.1 | 100.0 |
| | 0.01 | 94.0 |
| | 0.001 | 34.7 |

TABLE 2-continued

| Active ingredients | Conc. (%) | Inhibitory rate against 5α-reductase (%) |
|---|---|---|
| *Coptis chinensis* | 0.1 | 100.0 |
| | 0.01 | 44.9 |
| Azelaic acid | 1.0 | 100.0 |
| | 0.1 | 19.8 |

TABLE 3

| Items | Inhibitory rate against 5α-reductase depending on conc. (%) | | |
|---|---|---|---|
| | 0.1% | 0.05% | 0.01% |
| *Biota orientalis:Cavalia gladiata*(50:50) | 100 | 100 | 35.2 |
| *Biota orientalis:Coptis chinensis*(50:50) | 100 | 100 | 46.9 |
| *Cavalia gladiata:Coptis chinensis* (50:50) | 100 | 100 | 31.7 |
| *Cavalia gladiata:Biota orientalis:Coptis chinensis* (34:33:33) | 100 | 100 | 66.8 |
| *Cavalia gladiata:Biota orientalis:Coptis chinensis* (70:20:10) | 100 | 100 | 92.6 |

As shown in Table 2, each of three different types of extract (*Cavalia gladiata, Biota orientalis* and *Coptis chinensis*) is revealed to exhibit the inhibitory effect against the activity of 5α-Reductase. In addition, when at least two different kinds of extracts were mixed at a suitable ratio and dissolved in 70% ethanol to make 0.1, 0.05 and 0.01% (w/v) of extracts, the extract to be examined showed a significantly higher inhibitory effect against the activity of 5α-Reductase even at a low concentration as shown in Table 3, compared to that of extract containing single kind of extract. These results represent that the mixed extract at a suitable ratio shows a synergistic inhibitory effect against the activity of 5α-Reductase. It would be understood by one skilled in the art that the present compositions exhibiting a synergistic inhibitory effect against the activity of 5α-Reductase are not limited to those indicated previously.

EXAMPLE 3

Evaluation of Antimicrobial Activity Against Acne Pathogen

The examination on antimicrobial activity of three extracts (*Cavalia gladiata, Biota orientalis* and *Coptis chinensis*) was performed in such a manner that an acne pathogen (*Propionibacterium acnes*) that was cultured in liquid medium was treated with a predetermined concentration of extract powderized by freeze drying and then cultured in an anaerobic incubator, followed by measuring a minimum inhibitory concentration (MIC) against an acne pathogen (*Propionibacterium acnes*). The overall procedure is as follows:

The acne pathogen (*Propionibacterium acnes*) was cultured at 37° C. for 3 days in reinforced clostridial medium and then continued to subculture until showing significant activity.

First, in a liquid culture method, 10 ml of reinforced clostridial medium were introduced to screw cap tube and sterilized for 20 min at 121° C. After sterilization, 0.5 ml of liquid paraffin sterilized separately was added dropwise on the liquid medium to protect the contact with oxygen. After cooling the medium, the microbe was inoculated into the medium and cultured at 37° C. for above 72 hr.

Second, in a solid culture method, 10 ml of the solid medium prepared by adding 0.1% agar to reinforced clostridial medium was introduced to a screw cap tube and sterilized at 121° C. for 20 min. After cooling the medium, the microbe was inoculated into the medium by use of inoculating platinum loop and stab-cultured for 72 hr at 37° C.

Third, in a plate culture method, the agar medium prepared and sterilized as a solid culture method was poured to a plate and cooled. After cooling and solidifying completely, the plate was placed in an anaerobic jar, 10 ml of water were introduced to complex gas ($CO_2$ 10.5%, $H_2$ 9.6%, $N_2$ 79.9%) and the lid was kept covered, followed by culturing at 37° C. for 72 hr.

1 ml of the medium containing *Propionibacterium acnes* subjected to a sufficient subculture was taken and inoculated into a medium containing 9 ml of reinforced clostridial medium, thereby obtaining 10-fold diluted culture medium. The same procedure was repeated to obtain between $10^{-1}$ and $10^{-5}$ 4-fold diluted culture media. Each of the homogeneous solutions containing *Cavalia gladiata, Biota orientalis, Coptis chinensis* and at least two combinations thereof was well dissolved in 10 ml of 70% ethanol to obtain 2-fold diluted solution. The solution was filtered for removing bacteria through 0.2 μm membrane filter. The reinforced clostridial-agar medium was sterilized and cooled to 50° C. and to it, the extract removed of bacteria by filtering was added to a concentration of 10 μg/ml-0.1 mg/ml. 1 ml of the diluted medium (medium of *Propionibacterium acnes* subject to subculture diluted to $10^{-1}$-$10^{-5}$) was dispensed in a petri dish and each agar medium having certain concentration was dispensed, followed by mixing and keeping it to stand for solidifying the agar medium. After solidification, the medium was placed in an anaerobic jar that in turn was equipped with gas-pak. Following culturing at 37° C. for 3 days, the number of colonies formed were counted and compared to that of a control group, and the inhibitory rate was calculated based on the results. The inhibitory rates against *P. acnes* are shown in Tables 4 and 5.

TABLE 4

| MIC to *P. acnes* | Concentration of extract (%) | | | | | |
|---|---|---|---|---|---|---|
| | 0.50 | 0.10 | 0.05 | 0.03 | 0.01 | 0.005 |
| *Cavalia gladiata* | –* | – | – | – | ± | + |
| *Biota orientalis* | – | – | – | ± | + | + |
| *Coptis chinensis* | – | – | – | – | – | ± |
| Benzoylperoxide | – | ±** | +*** | + | + | + |

*inhibition of growth
**pseudo-positive (의양성)
***positive

As shown in Table 4 demonstrating the antimicrobial activity against *P. acnes*, the antimicrobial activity could be observed at a low concentration (0.03%) of extract and the acne-causing bacteria was completely killed at a high concentration (above 0.1%), while each extract showed a little difference in its MIC against *P. acnes*. Therefore, it would be appreciated that the extract from oriental medicine of this invention shows a noticeable bacteriocidal effect on *P. acnes* even at an extremely low concentration.

TABLE 5

| Extracts | Antimicrobial activity according to various concentrations (%) | | | |
|---|---|---|---|---|
| | 0.1% | 0.05% | 0.01% | 0.005% |
| *Biota orentalis:Cavalia gladiata*(50:50) | 100 | 100 | 85.7 | 33.2 |
| *Biota orientalis:Coptis chinensis*(50:50) | 100 | 100 | 89.8 | 44.9 |
| *Cavalia gladiata:Coptis chinensis*(50:50) | 100 | 100 | 92.3 | 49.7 |
| *Cavalia gladiata:Biota orientalis:Coptis chinensis*(34:33:33) | 100 | 100 | 92.4 | 46.8 |
| *Cavalia gladiata:Biota orientalis:Coptis chinensis*(70:20:10) | 100 | 100 | 92.6 | 48.6 |

As shown in the results, the composition comprising at least two extracts obtained from *Cavalia gladiata, Biota orientalis* and *Coptis chinensis* at a certain ratio showed slightly increased antimicrobial activity compared to that comprising a single extract. In particular, the composition containing three different extracts obtained from *Cavalia gladiata, Biota orientalis* and *Coptis chinensis* at a certain ratio was observed to exhibit excellent antimicrobial activity and inhibitory effect against 5α-reductase at each concentration.

EXAMPLE 4

Evaluation of Inhibitory Activity to Hypercornification

All skin cells help to maintain skin homeostasis through suitable metabolic processes by controlling the rate of their proliferation and exfoliation. Therefore, the reproduction rate of skin could be indirectly examined by observing the exfoliation rate of stratum corneum that can be generally measured by evaluating the level of skin discoloration associated with keratolysis.

In evaluating the efficacy of extracts, the first screening for promoting keratolysis was performed using hairless mouse. Each extract sample was prepared by dissolving the dried powder extract prepared in Example 1 in 70% ethanol and the positive controls including glycolic acid or lactic acid were prepared as described above. The experiments were carried out as follows:

The skin of a hairless mouse was washed with 10% SDS for 30 min and then allowed its skin to dry for experiment. 0.4 ml of aqueous silver acetate liquid was covered with a hill top chamber and closed patch was performed for 30 min, followed by infiltrating with a photo-developing solution to blacken a portion of patch with silver acetate. The closed patch was further performed with each extract sample on the blackened portion and removed after about 24 hr. The coloring index before application of extract and discoloring index at 24 hr after removal were measured by means of calorimeter (The higher the discoloring index, the higher is the keratolysis effect)

TABLE 6

| Sample | Appearance of Exfoliation | Conc. of Extract applied (%) | | |
|---|---|---|---|---|
| | | 0.2 | 0.1 | 0.05 |
| Cavalia gladiata | Homogeneous | ++[1] | + | + |
| Biota orientalis | Homogeneous | +[2] | ±[3] | −[4] |
| Coptis chinensis | Homogeneous | ++ | ± | − |
| Glycolic acid | Heterogeneous | 2 wt % (pH 4) ++ | | |
| Lactic acid | Heterogeneous | 2 wt % (pH 4) ++ | | |

[1] significant discoloration,
[2] discoloration,
[3] slight discoloration,
[4] no change The secondary quantitative effect to promote karatolysis was performed by use of at least two different extracts obtained from *Cavalia gladiata, Biota orientalis* and *Coptis chinensis* dissolved in 70% ethanol solution that have been revealed to have efficacy in the first screening. Dihydroxy acetone, conventionally used as skin discoloring agent in self-tanning products, was used as a coloring agent. The experimental procedure is as follows:

20 persons aged at early twenties-mid thirties were selected and the inner parts of their forearms were selected as a test part. The inner part was measured in terms of skin brightness before coloring and then colored with 10% dihydroxy acetone in a hill top chamber. Following 24 hr, the colored part was observed with calorimeter and 0.4 ml of each of samples comprising at least two extracts dissolved in 70% ethanol with a concentration of 0.05%, 0.1% and 0.2%, respectively, was applied for 30 min twice a day, after which the part applied was observed daily with colorimeter. The value measured with colorimeter after 24 hr of dihydroxy acetone application was set 100 and the daily discoloring level was converted to %. The evaluation was executed with the period for the discolored part's returning to normal color.

Inhibitory rate on Hypercornification=[(control group−tested group)/control group]×100    Formula 2

TABLE 7

| Sample | Period for returning according to various concentrations (day) | | | Inhibitory rate (%) |
|---|---|---|---|---|
| | 0.2 wt % | 0.1 wt % | 0.05 wt % | |
| Control | | 19 | | — |
| Cavalia gladiata:Biota orientalis(50:50) | 10 | 13 | 16 | 15.8-47.4 |
| Cavalia gladiata:Coptis chinensis(50:50) | 10 | 12 | 14 | 26.3-47.4 |
| Biota orientalis:Coptis chinensis(50:50) | 11 | 13 | 15 | 21.0-42.1 |
| Cavalia gladiata:Biota orientalis:Coptis chinensis(34:33:33) | 9 | 11 | 14 | 26.3-52.6 |
| Cavalia gladiata:Biota orientalis:Coptis chinensis(70:20:10) | 9 | 11 | 13 | 31.6-52.6 |

As shown in Table 7, the mixed composition containing at least two extracts exhibited the inhibitory rate of 47.4-52.6 at a concentration of 0.2%, demonstrating that the extract of this invention is capable of turning the skin discoloration by dihydroxy acetone back to normal skin color in short period of time. The mixed composition comprising at least two extracts showed higher keratolysis effect than that containing single extract and in particular, the mixed composition containing three extracts, *Cavalia gladiata, Biota orientalis* and *Coptis chinensis* showed the highest inhibitory activity against hypercornification.

EXAMPLE 5

Anti-Inflammatory Effect

1) Carrageenan Foot Edema Method Using SD Rat

The extracts from *Cavalia gladiata, Biota orientalis, Coptis chinensis* and their mixture prepared in Example 1 were intraperitoneally administered, respectively, in an amount of 30 mg/kg. After 1 hr, 0.5 ml of 0.1% carrageenan solution was injected into the sole of a back foot to induce inflammation. The volume change of rat foot at the time of injection of carrageenan and 4-hr after administration was measured and the Inhibitory rate was calculated according to the Formula 3. The results are shown in Table 8.

Inhibitory rate (%)=[(1−$\Delta V_{treated\ group}$)/ $\Delta V_{control\ group}$)]×100 ($\Delta$V: volume change of foot)    Formula 3

TABLE 8

| Sample | Inhibitory rate (%) |
|---|---|
| Cavalia gladiata | 68.8 ± 12 |
| Biota orientalis | 46.0 ± 10 |
| Coptis chinensis | 62.3 ± 13 |
| Cavalia gladiata:Biota orientalis(50:50) | 63.1 ± 8 |
| Cavalia gladiata:Coptis chinensis(50:50) | 70.4 ± 15 |
| Cavalia gladiata:Biota orientalis:Coptis chinensis(34:33:33) | 75.8 ± 9 |
| Cavalia gladiata:Biota orientalis:coptis chinensis(70:20:10) | 78.4 ± 10 |
| Aspirin | 35.2 ± 6 |

2) Balb.c Ear Edema Test

To examine anti-inflammatory effect of the extracts, irritation-inducing substances, 5.0% benzalkonium chloride, 2.5% coroton oil and 3000 iu/g retinoic acid (negative control) were dissolved in 70% ethanol solution and its 0.3 mg/ear was topically applied to mouse ear (6 mice per group) in order to induce edema. At 15 min and 6 hr after induction of edema, respectively, each of the extract and controls (0.3 mg/ear) was topically applied to mouse ear. After 24 hr of application of irritation-inducing substances, the applied portion of the mouse was cut off with a punch and its weight was weighted. The edema extent was evaluated based on the mean value from the measurements with micrometer. The results are shown in Table 9.

TABLE 9

| Samples | Inhibitory rate on ear weight (%) | Inhibitory rate on ear thickness (%) |
|---|---|---|
| Cavalia gladiata | 49.2 | 53.8 |
| Biota orientalis | 28.8 | 30.6 |
| Coptis chinensis | 36.0 | 38.9 |
| Cavalia gladiata:Biota orientalis(50:50) | 34.1 | 35.3 |
| Cavalia gladiata:coptis chinensis(50:50) | 44.7 | 48.0 |
| Biota orientalis:Coptis chinensis(50:50) | 32.3 | 34.6 |

TABLE 9-continued

| Samples | Inhibitory rate on ear weight (%) | Inhibitory rate on ear thickness (%) |
|---|---|---|
| Cavalia gladiata:Biota orientalis:Coptis chinensis(34:33:33) | 46.0 | 54.2 |
| Cavalia giadiata:Biota orientalis:Coptis chinensis(70:20:10) | 45.3 | 58.6 |
| Glycyrrhizinic acid | 38.4 | 42.7 |
| Indomethacin | 45.6 | 52.0 |

$$\text{Inhibitory rate (\%)} = [(A-B)/A] \times 100 \quad \text{Formula 4}$$

A: mean value of ear thickness of control group (ear thickness after treatment of negative control–ear thickness with no treatment)

B: ear thickness of sample group (ear thickness after treatment of sample–ear thickness with no treatment)

As shown in Tables 8 and 9, the groups treated with extracts showed the inhibitory activity against edema similar to glycyrrhizinic acid and indomethacin as a positive control. In particular, extract from *Cavalia gladiata*, and mixed extract from *Cavalia gladiata*, *Biota orientalis* and *Coptis chinensis* exhibited excellent inhibitory effect against edema that is higher 110-200% than those of negative control solutions.

EXAMPLE 6

Evaluation of Alleviatory Effect on Comedo Using Ear of White

Rabbit

Test system—This test has been generally adopted for evaluation of treatment. New Zealand white male rabbits aged at 4-month and weighed 2-3 kg were purchased and mitigated for 1 week, of which only the healthy ones determined with naked eye were selected.

Test materials—For test groups, the powderized extracts (0.1% (w/v)) from *Cavalia gladiata, Biota orientalis, Coptis chinensis* and their mixture dissolved in 70% ethanol solution were used, respectively, 1.0% azelaic acid dissolved in 70% ethanol solution was used as a positive control and 70% ethanol solution per se was used as negative control.

Classification of test systems—Isopropyl myriatate (Sigma) was daily applied to both ears of rabbit for 2 weeks for inducing comedo. Rabbits observed with naked eye to show typical comedo were selected and classified to groups each of which was comprised of 6 rabbits in consideration of comedo severity. After 2 weeks of IPM administration, the appearance of rabbit ear was observed to show severe enlargement of hair follicle and comedo formation, severe hypercornification of epidermis and hair follicle and eschar formation and severe inflammation.

Administration method of test materials—Test groups and a positive control to the right ear and a negative control to the left ear of rabbit were administered once daily for 2 weeks in the amount of 0.5 ml and spread with a swab. After 2 weeks, both ears were evaluated.

<Observation with Naked Eye>

The standards for determination with naked eye were classified to 7 grades, 0, 0.5, 1.0, 1.5, 2.0, 2.5 and 3.0. The area of comedo was evaluated. The period for treatment of comedo was 2-week and the aggravation and alleviation of comedo were determined. The results are shown in Table 10.

<Standards for Determination with Naked Eye>

0: no difference compared to control 0.1: symptoms between 0 and 1

1: showing congestion, bleeding of capillary tube, slight cornification and enlargement of hair follicle 1.5: symptoms between 1 and 2

2: medium severity of cornification and enlargement of hair follicle 2.5: symptoms between 2 and 3

3: excessive severity of cornification and enlargement of hair follicle, showing typical comedo

TABLE 10

| Sample | Before administration (left ear) | After administration (right ear) | Inhibitory rate (%) |
|---|---|---|---|
| Cavalia gladiata | 1.76 ± 0.12 | 1.21 ± 0.08 | 31.3 |
| Biota orientalis | 1.74 ± 0.10 | 1.44 ± 0.12 | 17.2 |
| Coptis chinensis | 1.78 ± 0.09 | 1.18 ± 0.13 | 33.7 |
| Cavalia gladiata:Biota orientalis(50:50) | 1.73 ± 0.12 | 1.12 ± 0.09 | 35.3 |
| Cavalia gladiata:Coptis chinensis(50:50) | 1.69 ± 0.14 | 1.14 ± 0.09 | 32.5 |
| Biota orientalis:Coptis chinensis (50:50) | 1.62 ± 0.07 | 1.09 ± 0.14 | 32.7 |
| Cavalia gladiata:Biota orientalis:Coptis chinensis(34:33:33) | 1.76 ± 0.10 | 1.04 ± 0.08 | 40.9 |
| Cavalia gladiata:Biota orientalis:Coptis chinensis(70:20:10) | 1.79 ± 0.09 | 1.05 ± 0.11 | 41.3 |
| Azelaic acid | 1.58 ± 0.12 | 1.13 ± 0.14 | 28.5 |
| 70% ethanol | 1.76 ± 0.10 | 1.73 ± 0.09 | 1.7 |

<Observation with Image Analysis>

After the observation with naked eye, each test group was euthanized with sodium pentobarbital and its both ears were cut out, after which their tissues at basement were cleaved in a size of about 2.5×1.5 cm and immersed in warm water (50° C.) for 3 min. The epiderms from the tissues were detached, placed with inner side upward on slide glass, fixed and dried at room temperature. The image was observed with stereoscopic microscope (×20) and the number of comedo on tissue and its area was calculated with image analyzer. The results are shown in Table 11.

TABLE 11

| Sample | Before administration (left ear) Area of comedo/number (cm$^2$) | After administration (right ear) Area of comedo/number (cm$^2$) | Inhibitory rate (%) |
|---|---|---|---|
| Cavalia gladiata | 0.30 ± 0.02 | 0.16 ± 0.02 | 46.7 |
| Biota orientalis | 0.32 ± 0.01 | 0.23 ± 0.01 | 28.1 |
| Coptis chinensis | 0.30 ± 0.02 | 0.17 ± 0.02 | 43.3 |
| Cavalia gladiata:Biota orientalis(50:50) | 0.31 ± 0.02 | 0.16 ± 0.01 | 48.4 |
| Cavalia gladiata:Coptis chinensis(50:50) | 0.29 ± 0.01 | 0.19 ± 0.01 | 34.5 |
| Biota orientalis:Coptis chinensis(50:50) | 0.31 ± 0.02 | 0.17 ± 0.02 | 45.2 |

TABLE 11-continued

| Sample | Before administration (left ear) Area of comedo/ number (cm²) | After administration (right ear) Area of comedo/number (cm²) | Inhibitory rate (%) |
|---|---|---|---|
| Cavalia gladiata:Biota orientalis:Coptis chinensis(34:33:33) | 0.32 ± 0.01 | 0.11 ± 0.02 | 55.4 |
| Cavalia gladiata:Biota orientalis:Coptis chinensis(70:20:10) | 0.32 ± 0.01 | 0.11 ± 0.02 | 65.6 |
| Azelaic acid | 0.30 ± 0.02 | 0.18 ± 0.02 | 40.0 |
| 70% ethanol | 0.31 ± 0.01 | 0.30 ± 0.02 | 3.2 |

As represented in Table 11, the extracts showing higher comedo decreasing ratio (area/count ratio) than azelaic acid (40.0%) as a positive control were *Cavalia gladiata* (46.7%), *Coptis chinensis* (43.3%) and composition comprising at least two extracts. In particular, the extract comprising *Cavalia gladiata:Biota orientalis:Coptis chinensis* (70:20:10) was revealed to show 1.6-fold comedo decreasing ratio higher than that of a positive control. This experiment demonstrating comedo decreasing ratio represents that results from observation with naked eye and image analysis are similar each other.

Summarizing the experiments depending on the mechanisms of acne development, the present extracts were demonstrated to exhibit antimicrobial activity against acne-causing bacteria, *P. acnes*, inhibitory effect of excess production of sebum, lysis effect of comedo, inhibitory effect of hyper-cornification and anti-inflammatory effect as well as safety to skin.

EXAMPLE 7

Evaluation of Irritation to Human Skin

To test skin safety, the extracts of *Cavalia gladiata, Biota orientalis*, and *Coptis chinensis* and the mixed extract comprising at least two different oriental medicines that were elucidated to show the treatment and prevention efficacies against acne was prepared in a form of emulsion and the human skin irritation test (human patch test) was carried out by using them. 20 μl of test materials (10% patch base) prepared were added dropwise to a finn chamber, were washed with 70% ethanol and dried, and placed on the test part, the inner part of forearm of 30 healthy persons aged 20-30, followed by fixing with microporous tape. After application for 24 hr with patch, the patch was detached and the test part was marked with oil pen. The skin response after 30 min- and 24 hr-application was observed and evaluated with referring to the standard as below:

In Table 12, the mean responsiveness is classified to ± (1 point), + (2 points), ++ (3 points) and +++ (4 points). The standards for determination are grade 1 (no irritation range) ranking below 1, grade 2 (slight irritation range) ranking below 3, grade 3 (intermediate irritation range) ranking below 5 and grade 4 (strong irritation range) ranking above 5.

TABLE 12

| | 24 hr | | | | 48 hr | | | | Mean responsiveness | |
|---|---|---|---|---|---|---|---|---|---|---|
| Sample | ± | + | ++ | +++ | ± | + | ++ | +++ | (n = 30) | Grade |
| Acne emulsion base | 4 | – | – | – | – | – | – | – | 2.00 | 2 |
| Base + Cavalia* 0.3 wt % | 2 | – | – | – | – | – | – | – | 1.00 | 1 |
| Base + Biota** 0.3 wt % | 6 | – | – | – | – | – | – | – | 2.75 | 2 |
| Base + Coptis*** 0.1 wt % | 4 | – | – | – | – | – | – | – | 2.00 | 2 |
| Base + Cavalia 0.3 wt % + Biota 0.3 wt % | 4 | – | – | – | – | – | – | – | 2.00 | 2 |
| Base + Cavalia 0.3 wt % + Coptis 0.1 wt % | 3 | – | – | – | – | – | – | – | 1.50 | 2 |
| Base + Biota 0.3 wt % + Coptis 0.1 wt % | 4 | – | – | – | – | – | – | – | 2.00 | 2 |

*Cavalia gladiata
**Biota orientalis
***Coptis chinensis

As shown in Table 12, the acne emulsion base showed irritation level of safety range, all oriental medicines except for *Cavalia gladiata* (grade 1) exhibited irritation level of above grade 2. *Coptis chinensis* was tested at a lower concentration due to pigmentation.

EXAMPLE 8 AND COMPARATIVE EXAMPLE 1

Preparation of Emulsion

The mixed extract of *Cavalia gladiata, Biota orientalis* and *Coptis chinensis* exhibiting the highest comedo lysis and decreasing effects was formulated in a form of emulsion with ingredients and their amounts described in Table 13. The preparatory procedure is as follows:

TABLE 13

| Ingredients | Example 8 (wt %) | Com. Ex. (wt %) |
|---|---|---|
| 1. cetearyl alcohol | 5.00 | 5.00 |
| 2. polysorbate-60 | 0.80 | 0.80 |
| 3. dimethicone copolymer | 0.80 | 0.80 |
| 4. cyclomethicone | 4.00 | 4.00 |
| 5. hohoba oil | 2.00 | 2.00 |
| 6. distilled water | Up to 100 | Up to 100 |
| 7. Canavalia gladiata:Biota orientalis:Coptis chinensis(70:20:10) | 0.50 | absent |
| 8. methyl paraben | 0.20 | 0.20 |
| 9. 1,3-bulylene glycol | 8.00 | 8.00 |
| 10. carbomer | 0.15 | 0.15 |
| 11. xanthan gum | 0.05 | 0.05 |
| 12. polyacrylamide/C13-14 isoparaffin/laures-7 | 1.20 | 1.20 |

TABLE 13-continued

| Ingredients | Example 8 (wt %) | Com. Ex. (wt %) |
|---|---|---|
| 13. imidazolydinylurea | 0.20 | 0.20 |
| 14. triethanol amine | 0.15 | 0.15 |
| 15. perfume | 0.10 | 0.10 |

The raw materials (ingredients 1-5) present in oil phase were exactly weighed, introduced into additional oil phase tank and dissolved by heating at 75° C. The raw materials (ingredients 6-9) present in water phase were weighed and introduced into an emulsifying tank. The raw materials (ingredients 10-11) were weighed, wetted with distilled water and introduced into the emulsifying tank. The ingredients in the emulsifying tank were dissolved with heating at 75° C. The ingredients of oil phase were introduced into the emulsifying tank under vacuum and emulsified for 5 min at 75° C. using a homogenizer (3500 rpm) and a pedal mixer (25 rpm). To the tank, ingredient 12 was added and dispersed for 3 min. Ingredients 13 and 14 were dissolved and dispersed in small amount of distilled water and introduced into the tank for neutralization. After defoamation under vacuum and cooling to 50° C., perfume was added, dispersed and cooled down to 35° C., and the resultant composition was maturated to prepare emulsion.

EXAMPLE 9 AND COMPARATIVE EXAMPLE 2

Preparation of Patch

TABLE 14

| Ingredients | Example 9 (wt %) | Com. Ex. (wt %) |
|---|---|---|
| 1. Glycerine | 15.00 | 15.00 |
| 2. Polyarylic acid | 2.00 | 2.00 |
| 3. Acrylate copolymer | 2.00 | 2.00 |
| 4. Ammonium hydroxide | 0.40 | 0.10 |
| 5. Disodium-EDTA | 0.05 | 0.05 |
| 6. Tartaric acid | 0.20 | 0.20 |
| 7. Methyl paraben | 0.20 | 0.20 |
| 8. Ethanol | 1.00 | 1.00 |
| 9. Glycyrrhizinic acid dipotassium | 0.10 | 0.10 |
| 10. Perfume | 0.05 | 0.05 |
| 11. Cavalia gladiata:Biota orientalis:Coptis chinensis(70:20:10) | 0.50 | — |
| 12. Propylene glycol | 5.00 | 5.00 |
| 13. Distilled water | Up to 100 | Up to 100 |

Ingredients 1-6 were weighed, introduced into a dissolving tank and homogeneously agitated at room temperature to prepare a viscous solution. Ingredients 7-10 were dissolved at room temperature, introduced into the dissolving tank and homogeneously agitated. Ingredients 11-13 were heated to 60° C., dissolved and introduced in aliquots with small volume, thus giving gel for patch. The gel for patch comprising the ingredients was homogeneously coated at the amount of 700 g/m² on polyester film with siliconized adhesive layer in a size of 1 m×1 m by use of coating apparatus with applicator cap, to prepare nonporous polyethylene film. The multilayered laminate was cut in a form of circular patch with a diameter of 1.5 cm and introduced into pouch laminated film paper, low density polyethylene and aluminum, thereby finally preparing clinical patch.

EXAMPLE 10

Clinical Test with Emulsion and Patch

Example 8 and Comparative Example 1 (test group of 15 persons and control group of 15 persons), and Example 9 and Comparative Example 2 (test group of 15 persons and control group of 15 persons) were evaluated in terms of alleviation effect to acnes. To 60 healthy persons aged at tens-twenties with acne symptoms, the emulsion was topically applied twice daily (in the mornings and evenings) and the patch was applied once daily (applied in the evenings and removed in the next mornings) for 1 month, and the treatment and prevention effects of acne were evaluated. Prior to test, skin and acne condition of testes were scored and photographed. After 1-month of the application of emulsion and patch, the extent of prevention and treatment of acne was determined based on photos and observation with naked eye. The standards for determination are found in Table 15.

TABLE 15

| Grade | Standards for determination of skin conditions |
|---|---|
| 0 | Normal condition |
| 1 | Negligible comedo counts or no development of inflammation |
| 2 | Noticeable comedo counts and size but no development of inflammation |
| 3 | A small counts of inflammatory papule |
| 4 | Crystalline and inflammatory comedo with small counts and broad distribution |
| 5 | Papulosa nodus with small counts and size |
| 6 | Noticeable counts of inflammatory nodus |
| 7 | Highly noticeable counts of inflammatory nodus |
| 8 | Severe crystalline comedo |
| 9 | Severe vesicula and inflammatory nodus |

Grades were determined based on the standards for determination in Table 15, where the grade on acne condition of testee was decreased by above 3 grades, it was evaluated as excellent efficacy; the grade was decreased by 1-2 grades, it was evaluated as medium efficacy; the grade was not decreased, it was evaluated as no efficacy; and the grade was increased, it was evaluated as aggravation. Table 16 represents the clinical results of acne prevention and treatment using emulsion and patch of this invention with referring to the standards for determination.

TABLE 16

| Test group | | Excellent efficacy | Medium efficacy | No efficacy | Aggravation | Adverse effect |
|---|---|---|---|---|---|---|
| Emulsion | Test group | 12(80%) | 2(13.3%) | 0 | 0 | 1(6.7%) |
| | Control | 0 | 5(33.3%) | 9(60%) | 0 | 1(6.7%) |
| Patch | Test group | 11(73.3%) | 4(26.7) | 0 | 0 | 0 |
| | Control | 0 | 6(40%) | 9(60%) | 0 | 0 |

Summarizing the results in Table 16, the emulsion and patch comprising *Cavalia gladiata*, *Biota orientalis* and *Cop-*

*tis chinensis* exhibit improved prevention and treatment effects against acne as compared to those without them.

EXAMPLE 11

Toxicity Test

The extracts obtained from *Cavalia gladiata, Biota orientalis* and *Coptis chinensis* were tested in terms of toxicity as follows: the extract dissolved in dimethylsulfoxide (DMSO) was diluted with water and administered in the amount of 100 mg/kg to each mouse (10 mice per group), followed by observation for 7 days. No mouse was dead.

As described previously, the present topical formulation comprising extract obtained from at least one oriental medicine selected from the group consisting of *Cavalia gladiata, Biota orientalis* and *Coptis chinensis*, are extremely effective in prevention and treatment of acnes through inhibition of the activity of 5α-reductase, antimicrobial activity against *P. acnes*, anti-inflammatory action, inhibition of comedo formation and keratolysis.

What is claimed is:

1. A method for treating acne, comprising administering to a subject in need of such treatment a topical formulation comprising extract obtained from two different kinds of oriental medicine, wherein said extract comprises 0.01-10 wt % of *Cavalia gladiata* and 0.01-10 wt % of *Biota orientalis;* 0.01-10 wt % of *Cavalia gladiata* and 0.001-5 wt % of *Coptis chinensis*; or 0.01-10 wt % of *Biota orientalis* and 0.001-5 wt % of *Coptis chinensis*.

2. A method for treating acne, comprising administering to a subject in need of such treatment a topical formulation comprising extract obtained from three different kinds of oriental medicine, wherein said extract comprises 0.01-10 wt % of *Cavalia gladiata* and 0.01-10 wt % of *Biota orientalis* and 0.001-5 wt % of *Coptis chinensis*.

3. The method according to claim 1, wherein said formulation is in the form of emulsion, gel, pack, cosmetic liquid or soap for cosmetics, ointments or patches for pharmaceuticals.

4. The method according to claim 2, wherein said formulation is in the form of emulsion, gel, pack, cosmetic liquid or soap for cosmetics, ointments or patches for pharmaceuticals.

5. The method according to claim 1 or 2, wherein administration of said topical formulation induces an inhibitory effect on 5α-reductase, an antimicrobial activity against acne pathogen, an inhibitory activity to hypercornification, an alleviatory effect on comedo, or a combination thereof.

* * * * *